Figure 1:
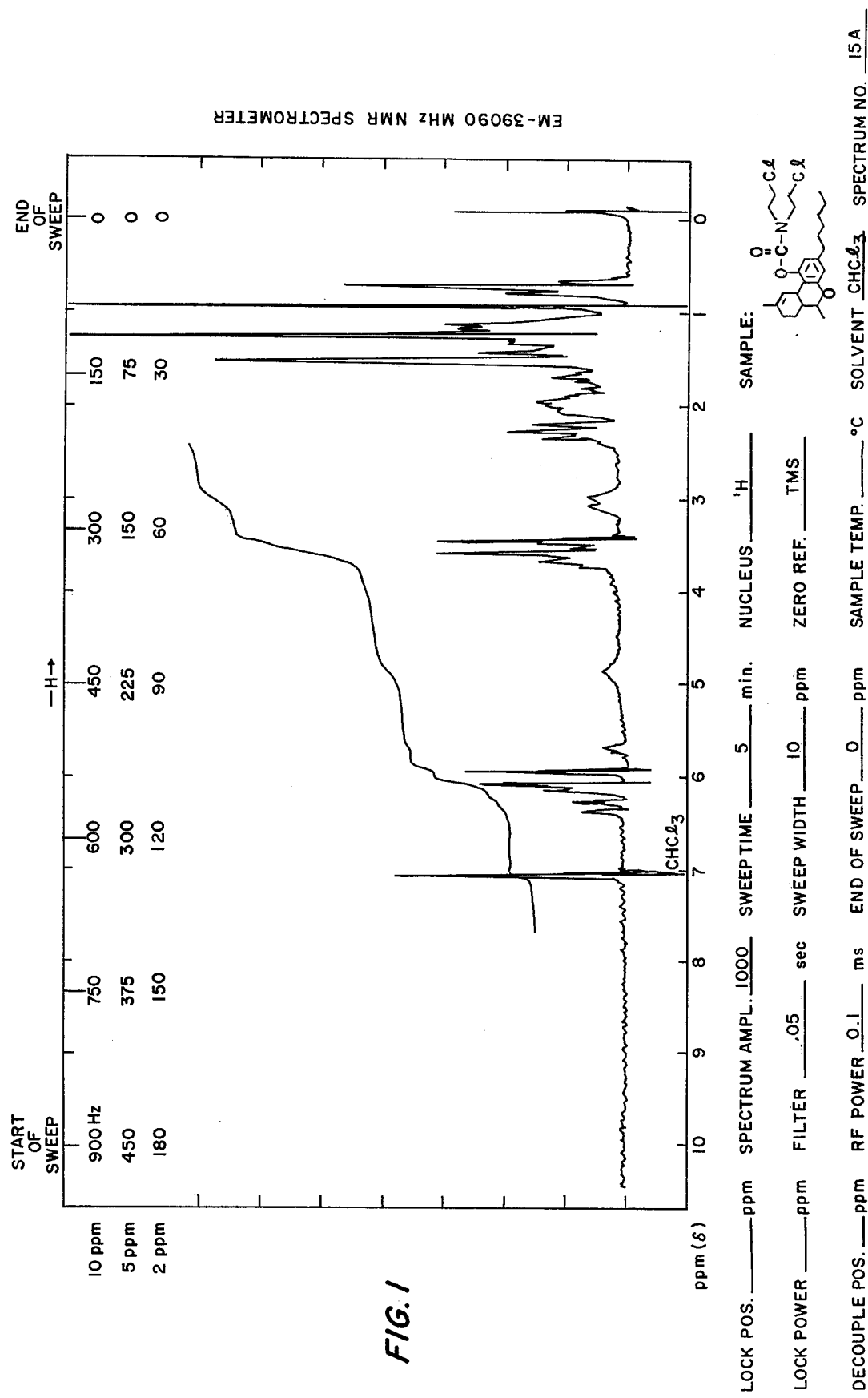

United States Patent [19]

Kaplan

[11] 4,327,028
[45] Apr. 27, 1982

[54] COMPOSITION OF MATTER
[75] Inventor: Norman C. Kaplan, Del Mar, Calif.
[73] Assignee: Calcol, Inc., Cleveland, Ohio
[21] Appl. No.: 934,465
[22] Filed: Aug. 17, 1978
[51] Int. Cl.$^3$ ............................................. C07D 311/78
[52] U.S. Cl. ................................... 260/345.3; 424/283
[58] Field of Search ....................................... 260/345.3
[56] References Cited
U.S. PATENT DOCUMENTS 3,639,427 2/1972 Razdan et al. .................... 260/345.3
4,036,857 7/1977 Razdan et al. .................... 260/345.3
4,051,152 9/1977 Razdan et al. .................... 260/345.3
4,133,819 1/1979 Johnson ............................. 260/345.3

Primary Examiner—Nicky Chan
Attorney, Agent, or Firm—Bruno J. Verbeck

[57]    ABSTRACT

A new compound, Δ-9-N-N-Bis-dichloroethyl carbamate Tetrahydrocannabinol, useful as a therapeutic agent particularly because of its efficacy against tumor cells of all types, having anti-tumor properties, and autoimmune diseases, having immune suppressive effects. The compound can be injected at therapeutic dosages in a vehicle of ethanol or an emulsion of mineral oil and water of Freund's complete or incomplete adjuvant or in olive oil.

1 Claim, 1 Drawing Figure

COMPOSITION OF MATTER

BACKGROUND OF THE INVENTION

Among the compositions that are currently used to carry anti-tumor compounds to tumor cells, acting as a site-specific anti-tumor drug, are compositions of nitrogen mustard and various steroid hormones, typified by the compound of normustine and oestradiol. Such compounds utilize the concept of steroid hormones such as estrogen as a carrier of the inert cytotoxic agent directed to the target tissue where cleavage of the molecule by hydrolysis releases active normustine. With many compounds of this type, the use thereof is accompanied by such undesirable side effects as hormonal side-effects, emetic properties, and mood-depression which augment that depression which frequently accompanies traumatic illness such as cancer.

There is, accordingly, a present need for therapeutic agents utilizing the concept of a carrier and an inert cytotoxic agent which can be carried to the target tissue where cleavage of the molecule will release the cytotoxic agent, without the undesirable side effects heretofore associated with many of the presently used compositions.

SUMMARY OF THE INVENTION

The present invention is directed to a new composition which is useful as a therapeutic agent. In addition to its effectiveness against tumor cells, it is non-addictive, anti-emetic, and has mood-elevating properties which are desirable in the palliation of that depression which frequently accompanies traumatic illnesses such as cancer and the chemotherapy of it.

The compound of this invention, Δ-9-N-N-Bis-dichloroethyl carbamate Tetrahydrocannabinol, having the structural formula

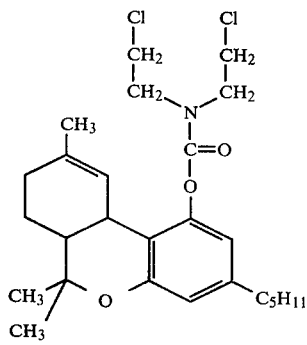

may be prepared by a variety of methods, which will be described in full detail hereinafter.

In general, that method comprises reacting Δ-9-Tetrahydrocannabinol with a nor-nitrogen mustard, such as N-chloroformyl bis(2-chloroethylamine), whereby the nitrogen mustard is bound to the phenolic hydroxyl.

By way of illustration of my invention, reference is made to the following examples, it being understood that these are illustrative only.

EXAMPLE 1

A quantity of Δ-9-Tetrahydrocannabinol (Mol. Wt. 314.45) in ethanol was concentrated to a constant weight in vacuo leaving 0.200 grams of a gummy residue. It was immediately dissolved in 6.0 ml of freshly distilled (from KOH) pyridine and stirred under nitrogen with cooling (in an ice bath).

0.225 grams of N-chloroformyl bis(2-chloroethylamine) (Mol. Wt. 190.48), at refrigerating temperature, was added dropwise via syringe over a six minute period using 1 ml of pyridine to ensure complete transfer.

The reaction mixture was stirred at room temperature under nitrogen for a total of 72 hours; ice was added, about 25 grams, and the solution stirred and transferred to a separatory funnel. Ethyl acetate (40, 30, 30 ml) was used to extract the yellow solution three times. Aqueous layer 13-A.

The combined ethyl acetate layers were:

| | |
|---|---|
| washed with 1N NAOH (2 × 20 ml) | Aqueous layer 13-B |
| washed with saturated salt solution (1 × 20 ml) | Combined Aqueous layer 13-C |
| washed with 1N HCl (2 × 20 ml) | | washed with a saturated salt solution, and then dried over anhydrous magnesium sulfate (5 hours).

The aqueous layers, 13-A, 13-B, and 13-C were back extracted with chloroform to give a second solution.

The ethyl acetate sample was evaporated to dryness to give 0.2759 grams (91% yield) of a pale yellow oil. To remove trace amounts of ethyl acetate, the sample was redissolved in chloroform, filtered, and evaporated to give 0.2746 g of product.

The identity of the compound was established by means of an EM-390 90 MHz NMR Spectrometer, as shown in FIG. 1.

The N Formyl chloride used in the foregoing reaction with Δ-9-Tetrahydrocannabinol was prepared as follows:

21.0 grams of N,N bis(2-chloroethyl)amine. HCl, (Mol. Wt. 178.49) in the form of an ice cold solution (21.0 grams, 0.118 moles) in 20 ml of water, is shaken in a separatory funnel with cold KOH (6.8 grams) in water (12 ml). The oil is taken up in benzene (ca 350 ml), dried over magnesium sulfate, and filtered to give benzene solution of N-(chloroformyl bis(B-chloroethyl)amine B.p. 114°–116°

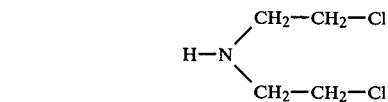

to give 400 ml of solution.

The solution above (kept cold) is added dropwise to a solution of phosgene in benzene (COCl₂ in C₆H₆).

7.3 grams of phosgene=0.07 moles=17.5 ml of a 4M solution diluted to 100 cc in benzene, keeping the temperature below 10° C.

The solution was allowed to stand for several hours and then reacted as follows:

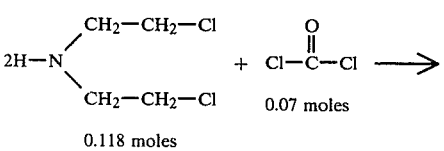

-continued

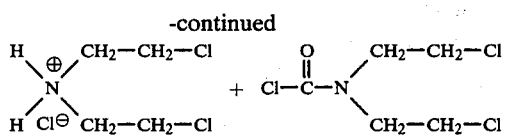

The hydrochloride was removed by filtration, then rotary evaporated, benzene and distilled under pressure.

The other reactant used in preparing the novel compound of my invention, Δ-9-tetrahydrocannabinol may be obtained from the National Institute of Drug Abuse; it may be extracted from the leaves of Cannabis Sativa by procedures well known to those skilled in the art, or it can be synthesized according to the method of Mechoulam, described in the *Journal of American Chemical Society*, 87:14, pp. 3272–3275, July 20, 1965; or Taylor, Leonard and Shvo [*J. Am. Chem. Soc.* 88:367 (1967)].

EXAMPLE 2

Δ-9-Tetrahydrocannabinol in solution in 30 ml of dioxane with 0.04 mole of phosgene in 15 ml of $COCl_2$ (benzene) was added dropwise with stirring at room temperature to produce Δ-9-Chloroformate Tetrahydrocannabinol, which after standing overnight, was concentrated (almost to crystallization) with the addition of 15 ml of petroleum ether. Then, N,N-Bis(2-chloroethyl)amine from 3 gm. (0.016 mole) of the hydrochloride in 30 ml of benzene was added to 0.0056 mole of Δ-9-Chloroformate Tetrahydrocannabinol in 25 ml of benzene with stirring at room temperature overnight. The mixture was filtered, the solvent was removed under reduced pressure, and the oily residue dissolved in 25 ml of EtOH.

It is, of course, to be understood that the foregoing examples are illustrative only and that numerous changes can be made in the ingredients, conditions, and the proportions set forth without departing from the spirit of the invention as set forth in the appended claims.

What is claimed is:

1. Δ-9-N,N-Bis-dichloroethyl carbamate Tetrahydrocannabinol having the formula:

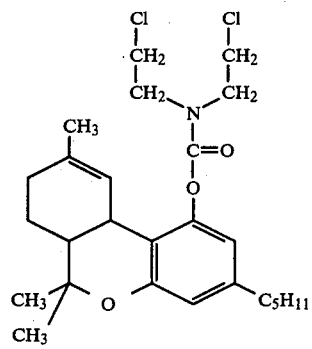

* * * * *